US010092236B2

(12) United States Patent
Johnson et al.

(10) Patent No.: US 10,092,236 B2
(45) Date of Patent: Oct. 9, 2018

(54) EMERGENCY MEDICAL SERVICES SMART WATCH

(71) Applicant: ZOLL Medical Corporation, Chelmsford, MA (US)

(72) Inventors: Guy R. Johnson, Gloucester, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 14/988,000

(22) Filed: Jan. 5, 2016

(65) Prior Publication Data

US 2016/0128626 A1    May 12, 2016

Related U.S. Application Data

(63) Continuation-in-part of application No. 14/036,313, filed on Sep. 25, 2013.

(60) Provisional application No. 62/100,707, filed on Jan. 7, 2015.

(51) Int. Cl.
*A61B 5/00* (2006.01)
*A61H 31/00* (2006.01)
(Continued)

(52) U.S. Cl.
CPC ............ *A61B 5/486* (2013.01); *A61B 5/0002* (2013.01); *A61B 5/021* (2013.01); *A61B 5/0205* (2013.01); *A61B 5/02108* (2013.01); *A61B 5/02438* (2013.01); *A61B 5/681* (2013.01); *A61B 5/7275* (2013.01); *A61B 5/742* (2013.01); *A61H 31/005* (2013.01); *A61H 31/007* (2013.01); *A61N 1/39* (2013.01); *G06F 19/3481* (2013.01); *G16H 40/63* (2018.01); *A61B 5/002* (2013.01); *A61B 5/7445* (2013.01); *A61H 2201/0184* (2013.01); (Continued)

(58) Field of Classification Search
CPC ......... A61B 5/486; A61B 5/681; A61B 5/742; A61B 5/4836; A61B 5/7445; A61H 31/005; A61H 31/007; A61H 2230/04; A61H 2201/501; A61N 1/3993; G06F 19/3406
USPC ........................................................ 600/301
See application file for complete search history.

(56) References Cited

U.S. PATENT DOCUMENTS 4,589,420 A    5/1986    Adams et al.
4,732,158 A    3/1988    Sadeh
(Continued)

FOREIGN PATENT DOCUMENTS

WO    WO93/016636    9/1993

*Primary Examiner* — Nathan J Jenness
(74) *Attorney, Agent, or Firm* — ZOLL Medical Corporation

(57) ABSTRACT

A system comprising: a wrist-worn device configured to be worn on the wrist of a rescuer performing cardiopulmonary resuscitation (CPR), the wrist-worn device including: one or more sensors coupled with the wrist-worn device, the one or more sensors being configured to sense one or more parameters indicative of a fatigue level of the rescuer; and a sensor interface configured to provide the sensed parameters to one or more external computing devices via an interface; and a wearable computing device configured to be worn by a rescuer, the wearable computing device including: a device interface for receiving information related to CPR; and a display for displaying an indication of the received information.

40 Claims, 8 Drawing Sheets

(51) Int. Cl.
  *A61B 5/0205* (2006.01)
  *A61B 5/021* (2006.01)
  *A61B 5/024* (2006.01)
  *A61N 1/39* (2006.01)
  *G06F 19/00* (2018.01)
  *G16H 40/63* (2018.01)

(52) U.S. Cl.
  CPC .... *A61H 2201/10* (2013.01); *A61H 2201/501* (2013.01); *A61H 2201/5007* (2013.01); *A61H 2201/5012* (2013.01); *A61H 2201/5046* (2013.01); *A61H 2201/5048* (2013.01); *A61H 2201/5084* (2013.01); *A61H 2201/5097* (2013.01); *A61H 2230/04* (2013.01); *A61H 2230/06* (2013.01); *A61H 2230/205* (2013.01); *A61H 2230/207* (2013.01); *A61H 2230/30* (2013.01); *A61H 2230/42* (2013.01); *A61N 1/3993* (2013.01)

(56) References Cited

U.S. PATENT DOCUMENTS

| | | | |
|---|---|---|---|
| 4,938,228 A | 7/1990 | Righter et al. | |
| 5,191,891 A | 3/1993 | Righter | |
| 5,333,616 A | 8/1994 | Mills et al. | |
| 5,351,695 A | 10/1994 | Mills et al. | |
| 5,670,944 A | 9/1997 | Myllymaki | |
| 6,491,647 B1 | 12/2002 | Bridger et al. | |
| 7,272,435 B2 | 9/2007 | Rowlandson | |
| RE40,116 E | 2/2008 | Engstrom | |
| 7,996,187 B2 | 8/2011 | Nanikashvilli et al. | |
| 8,068,900 B2 | 11/2011 | Xue | |
| 2003/0155389 A1* | 8/2003 | Swartzentruber | A44C 5/12 224/164 |
| 2004/0267325 A1* | 12/2004 | Geheb | A61B 5/11 607/5 |
| 2006/0142808 A1* | 6/2006 | Pearce | A61N 1/39 607/5 |
| 2008/0171311 A1* | 7/2008 | Centen | G09B 23/288 434/265 |
| 2009/0112630 A1* | 4/2009 | Collins, Jr. | G06F 19/327 705/3 |
| 2011/0117529 A1* | 5/2011 | Barash | G09B 23/288 434/265 |
| 2011/0288877 A1 | 11/2011 | Ofek et al. | |
| 2012/0092161 A1 | 4/2012 | West | |
| 2012/0123223 A1* | 5/2012 | Freeman | G06F 19/3406 600/301 |
| 2012/0123224 A1* | 5/2012 | Packer | G06F 19/327 600/301 |
| 2014/0081179 A1 | 3/2014 | Moore-Ed | |

* cited by examiner

EMERGENCY MEDICAL SERVICES SMART WATCH

CLAIM OF PRIORITY

This application claims priority under 35 USC § 119(e) to U.S. Patent Application Ser. No. 62/100,707, filed Jan. 7, 2015, and is a continuation-in-part of and claims priority under 35 USC § 120 to U.S. patent application Ser. No. 14/036,313, filed on Sep. 25, 2013, the entire contents of both of which are hereby incorporated by reference.

TECHNICAL FIELD

This document relates to cardiac resuscitation and, in particular, to systems and techniques for assisting rescuers in performing cardio-pulmonary resuscitation (CPR).

BACKGROUND

CPR is a process by which one or more rescuers may provide chest compressions and ventilation to a victim who has suffered an adverse cardiac event—by popular terms, a heart attack. During the first five to eight minutes after CPR efforts begin, chest compressions are considered to be the most important element of CPR because chest compressions help maintain circulation through the body and in the heart itself.

CPR may be performed by a team of one or more rescuers, particularly when the rescuers are professionals, such as emergency medical technicians (EMTs) on an ambulance crew. One rescuer can provide the chest compressions while another can provide and time their ventilations of the victim to match the chest compressions according to the appropriate CPR protocol. When professionals such as EMTs provide the care, ventilation is more likely to be provided via a ventilation bag that a rescuer squeezes rather than by mouth-to-mouth. CPR can be performed in conjunction with shocks to the patient provided by an external defibrillator, such as from an automatic external defibrillator (AED) that is designed to be used by laypeople. Such AEDs often provide audible information to rescuers, such as "push harder" (when the rescuer is not performing chest compressions forcefully enough), "stop CPR," "stand back" (because a shock is about to be delivered), and so on. In order to determine how chest compressions are being performed, certain defibrillators may obtain information from one or more accelerometers (such as in the CPR D PADZ, CPR STAT PADZ, and ONE STEP pads made by ZOLL MEDICAL of Chelmsford, Mass.) that can be used to compute depths of chest compression (e.g., to determine that the compressions are too shallow to be effective and to thus cause the verbal cue "push header" to be spoken by the defibrillator).

SUMMARY

This document describes systems and techniques that may be used to help manage the response to an emergency medical event. Feedback is provided to a rescuer (e.g., a rescuer performing CPR) via a smart watch platform or other wrist-worn device. For example, CPR feedback, such as rate, depth, and CPR interval time, can be displayed on a high pixel density and curved form factor device worn on the rescuer's wrist. Additional feedback, such as release velocity, victim heart rate, inspired carbon dioxide, and/or ventilation prompts, can additionally or alternatively be displayed on the high pixel density and curved form factor device. Other patient information such as ECG or other measured parameters can additionally be displayed. One example of such a high pixel density and curved form factor display is an indium gallium zinc oxide-based display. The wrist-worn device can communicate with a defibrillator or other computing device using a short-range wireless protocol that allows for the combination of high-speed communications and low standby power, such as the Bluetooth 4 protocol.

This document also describes systems and techniques that may be used to help manage the work by teams of rescuers who are responding to a victim or person in need of emergency assistance. For example, typically, such teams include a pair of rescuers, where the first of the rescuers performs CPR chest compressions on the victim and the other performs ventilations, either by mouth-to-mouth techniques or using a flexible ventilator bag. Frequently, a good heartbeat cannot be established quickly for the victim so CPR must be carried out for many minutes in order to maintain perfusion of blood in the victim. In such situations, rescuers can tire after only a minute or two of providing chest compressions, so certain protocols call for the rescuers to switch roles periodically. The systems and techniques discussed here are implemented with recognition that different people have different levels of stamina for performing chest compressions and other components of CPR, such as ventilating a victim or administering drugs to the victim. As a result, the techniques discussed here monitor the physical state of the rescuer, (e.g., by monitoring the heart rate or blood pressure of the rescuer) and tell the rescuers to switch out when the rescuer data indicates that the CPR might be, or would be, better performed by the other rescuer due to tiring of the initial rescuer. This feedback to switch rescuers is provided to a rescuer on a flexible, wrist-worn device, such as a smart watch.

In certain implementations, systems and techniques described herein may provide one or more advantages. For example, a patient may be provided with the best care that is available from the rescue team throughout a rescue episode. For example, a rescuer with greater stamina may be left performing chest compressions longer than another rescuer with less stamina, whereas, alternatively, they might have been allowed to perform for equal time periods, leading to a substandard performance caused by using techniques other than those described here. Also, the terms of each cycle may change as the rescue continues based on the level of physical exertion of the rescuer and the rescuer's physical stamina. Such adjustments may be dynamic and need not rely on a static timed schedule. The instructions to switch may also be provided in a clear and simple manner (and in a variety of manners, such as a visual display worn by the rescuer performing chest compressions), so that even rescuers in a high-stress environment can get the message. In addition, in certain implementations, the techniques described here can be implemented as part of an automatic external defibrillator (AED) or a professional defibrillator, or in a dual-mode defibrillator. As a result, the clinical performance of a rescuing team can be increased, and patient outcomes improved.

In one aspect, a system includes a wrist-worn device configured to be worn on the wrist of a rescuer performing cardiopulmonary resuscitation (CPR). The wrist-worn device includes one or more sensors coupled with the wrist-worn device. The one or more sensors are configured to sense one or more parameters indicative of a fatigue level of the rescuer. The wrist-worn device also includes a sensor interface configured to provide the sensed parameters to one or more external computing devices via an interface. The system also includes a wearable computing device configured to be worn by a rescuer. The wearable computing device includes a device interface for receiving information related to CPR, and a display for displaying an indication of the received information.

Implementations can include one or more of the following features.

In some implementations, the wrist-worn device includes a wrist-worn display formed of a flexible material configured to wrap around the wrist, and a controller arranged to receive information related to CPR from at least one of the sensors and external computing devices and display an indication on the wrist-worn display related to the received information.

In some implementations, the wearable computing device receives the information related to CPR from the wrist-worn device.

In some implementations, the wearable computing device receives the information related to CPR from one or more of the external computing device.

In some implementations, in response to sensing the one or more parameters indicative of a fatigue level of the rescuer, the device interface is configured to receive an indication to switch rescuers. The wearable computing device is configured to display an indication on the display related to the received indication to switch rescuers.

In some implementations, the wearable computing device includes wearable glasses.

In some implementations, the display is formed on at least one lens of the wearable glasses.

In some implementations, the wrist-worn device includes a band formed of multiple springy metal bands.

In some implementations, the one or more sensors include sensors configured to monitor at least one of a heart rate and blood pressure of the rescuer.

In some implementations, the system includes an electronic patient monitor. The system also includes a sensor interface on the electronic patient monitor arranged to receive input from one or more sensors that sense one or more parameters indicative of a CPR quality level. The system also includes a CPR monitor in the electronic patient monitor configured to use the input from the sensors to identify a quality parameter and to provide information associated with the quality parameter to the wrist-worn device.

In some implementations, the electronic patient monitor is part of an external defibrillator.

In some implementations, the CPR monitor includes a microprocessor connected to an electronic memory that stores instructions that, when executed, perform a process of identifying a quality parameter that reflects one or both of a depth of chest compressions and a rate of chest compression.

In some implementations, the display is configured to provide feedback to a rescuer indicating a way to improve a CPR component.

In some implementations, the wrist-worn device includes a memory configured to store a unique identifier associated with the wrist-worn device.

In some implementations, the wrist-worn device is configured to power on when the wrist-worn device wraps around the wrist.

In some implementations, the system includes a heads-up device to provide feedback to a user related to CPR performance based on the one or more parameters associated with the CPR performance.

In another aspect, a system includes a wrist-worn device configured to be worn on the wrist of a rescuer performing CPR. The wrist-worn device includes one or more sensors coupled with the wrist-worn device. The one or more sensors are configured to sense one or more parameters indicative of a fatigue level of the rescuer. The wrist-worn device also includes a sensor interface to provide the sensed parameters to one or more external computing devices via an interface. The system also includes a heads-up device configured to be viewed by a rescuer. The heads-up device includes a device interface for receiving information related to CPR, and a display for displaying an indication of the received information.

Implementations can include one or more of the following features.

In some implementations, the display is configured to present the indication via a projected image.

In another aspect, a method includes monitoring, with a sensor coupled with a wrist-worn device, one or more parameters indicative of a status of a user wearing the wrist-worn device. The method also includes determining a fatigue score related to a level of fatigue of the user. The method also includes determining whether the user is exhibiting fatigue based on the fatigue score. The method also includes providing an indication to the user that a different user should perform a CPR component.

Implementations can include one or more of the following features.

In some implementations, the method includes repeating the actions of monitoring, determining, and providing, while multiple different users are instructed to perform the CPR component.

In some implementations, the CPR component includes chest compressions.

In some implementations, the method includes sending, to a wearable computing device worn by the user, information related to the CPR component.

In some implementations, the wearable computing device includes wearable glasses.

In some implementations, a display is formed on at least one lens of the wearable glasses.

In some implementations, the information related to the CPR component includes one or more parameters indicative of a quality level of the CPR component. The one or more parameters include one or more of depth of compression and rate of compression. Determining the fatigue score includes determining the fatigue score based on the one or more parameters. The one or more parameters also indicate a physical status of the user.

In some implementations, the method includes generating a chest compression quality score based on one or both of the rate of compression and the depth of compression. The method includes providing an indication of the chest compression quality score to the wearable computing device.

In some implementations, the method includes providing periodic feedback to the user by causing information representing one or both of chest compression depth and chest compression rate to be presented on the display.

In some implementations, the status includes a physical status.

In some implementations, the method includes transmitting the fatigue score to a central management system.

In another aspect, a method includes receiving, from a sensor coupled with a wrist-worn device, one or more parameters indicative of a status of a user wearing the wrist-worn device. The method also includes determining, based on the one or more parameters, a fatigue indication associated with a fatigue level of the user. The method also includes sending, to a wearable computing device, information to cause the wearable computing device to provide an indication to the user that a different user should perform a CPR component.

Implementations can include one or more of the following features.

In some implementations, the CPR component includes chest compressions.

In some implementations, the wearable computing device includes wearable glasses.

In some implementations, the method includes receiving one or more parameters indicative of a quality level of the CPR component. The one or more parameters include one or more of depth of compression and rate of compression. Determining the fatigue indication includes determining the fatigue indication based on the one or more parameters. The fatigue indication is indicative of a physical status of the user.

In some implementations, the method includes receiving information related to one or both of a depth of chest compressions and a rate of chest compressions. The method also includes generating a chest compression quality score based on one or both of the depth of chest compressions and the rate of chest compressions. The method also includes sending, to the wearable computing device, information to cause the wearable computing device to display information representing the chest compression quality score.

In some implementations, the status includes a physical status.

In another aspect, a computer readable medium stores instructions for causing a computing system to monitor, with a sensor coupled with a wrist-worn device, one or more parameters indicative of a status of a user. The instructions also cause the computing system to determine a fatigue score related to a level of fatigue of the user of the wrist-worn device. The instructions also cause the computing system to determine that the user is exhibiting fatigue based on the fatigue score. The instructions also cause the computing system to provide an indication that a user other than the user of the wrist-worn device should perform a CPR component.

Implementations can include one or more of the following features.

In some implementations, the instructions cause the system to cyclically repeat the actions of monitoring, determining, and providing, while multiple different users are instructed to perform the CPR component.

In some implementations, the CPR component includes chest compressions.

In some implementations, the indication is provided to a wearable computing device that includes wearable glasses.

In some implementations, a display is formed on at least one lens of the wearable glasses.

Other features and advantages will be apparent from the description and drawings, and from the claims.

DETAILED DESCRIPTION

This description discusses systems and techniques for guiding the provision of care to a patient, such as the provision of CPR to a victim of cardiac arrest. For example, a portable electronic defibrillator may be provided to rescuers and may include common features for delivering defibrillating energy (a shock) to a victim of cardiac arrest through electrodes that may be placed on the torso of the victim. The defibrillator may also be provided with a mechanism for sensing the manner in which CPR chest compressions are performed on the victim, such as a puck or similar item that includes an accelerometer, which may be placed under the hands of the person performing chest compressions and on top of the sternum of the victim. The defibrillator may use information from such an item to identify the depth and rate of chest compressions that are being performed by a rescuer. Feedback can be provided to the rescuer via a curved form factor display worn on the wrist of the rescuer such as a smart watch with an indium gallium zinc oxide high pixel density display.

In some embodiments, the wrist-worn device can include one or more sensors to track the physiological state of the rescuer by monitoring factors of the rescuer such as pulse and blood oxygen level. This information can be used to assess the fatigue level of the rescuer and make a determination as to when multiple rescuers at the scene of the rescue event should switch performing CPR. When the defibrillator makes a determination that the rescuer is suffering from fatigue, the defibrillator may provide an indication to that rescuer that he or she should step away and allow another rescuer to perform chest compressions for a time. Such an indication can be provided through the smart watch worn by the rescuer. For example, where there are two rescuers, the second rescuer may have been providing ventilation to the victim using a ventilation bag and may be simultaneously prompted to change and provide chest compressions, while the first rescuer takes over operation of the bag.

Figure 1:
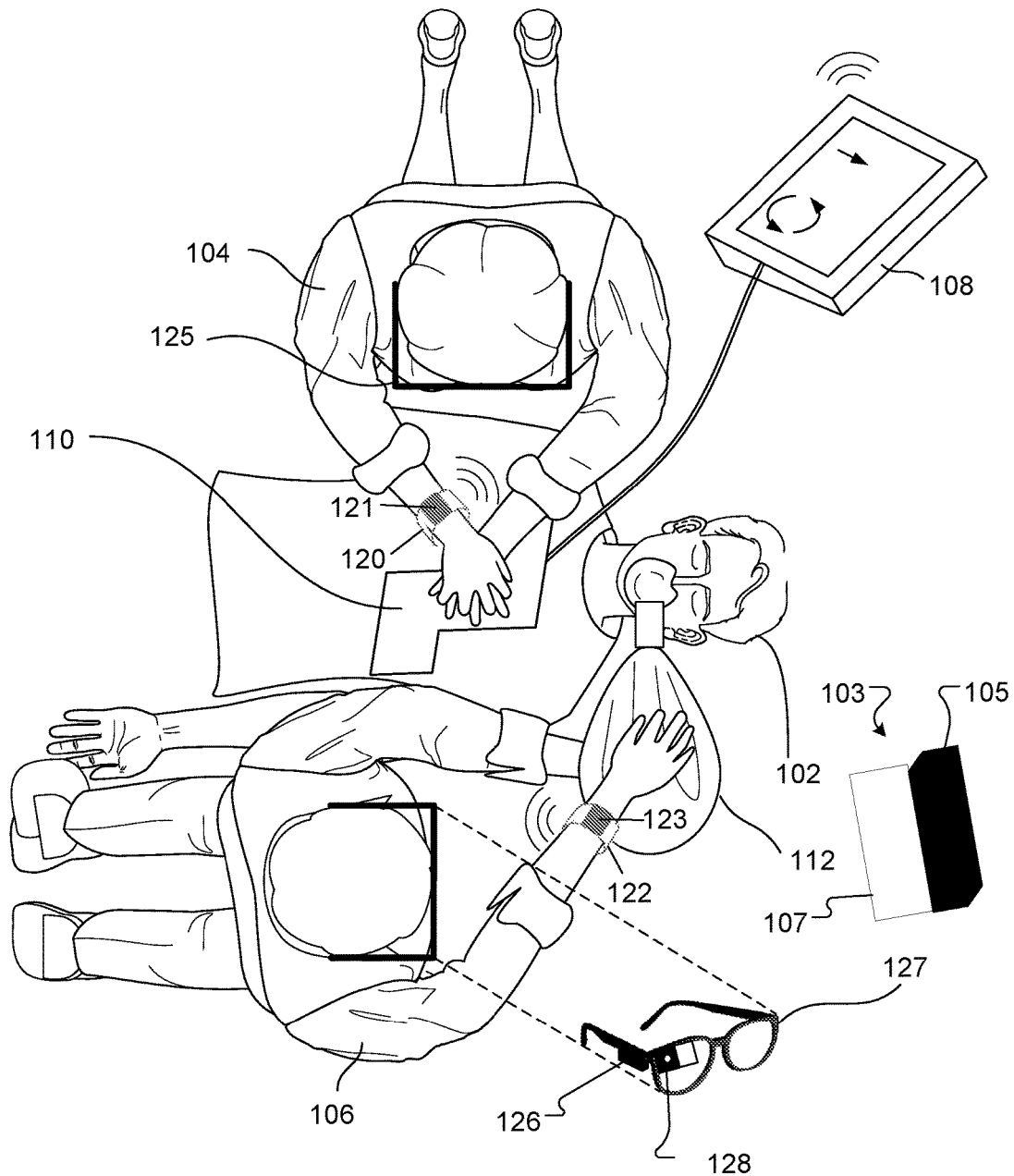
FIG. 1 is an overhead view of rescuers performing CPR on a victim using an electronic system that instructs them in their performance of the CPR.

FIG. 1 is an overhead view of rescuers 104, 106 performing CPR on a victim 102 using an electronic system that instructs them in their performance of the CPR. Each of the rescuers 104, 106 wears a wrist-worn device 120, 122, such as a smart watch, with a curved form factor display 121, 123. The wrist-worn devices 120, 122 include one or more sensors to sense one or more activities associated with the CPR performance and may also provide feedback to the rescuers performing the CPR on the victim 102. In this instance, each of the rescuers 104, 106 also wears a wearable computing devices 125, 127 in the form of a pair of glasses. The wearable computing devices 125, 127 provide feedback to the rescuers performing CPR on the victim 102. For example, a device interface 126 (integrated into the wearable computing device 127) can receive information from the wrist-worn devices 120, 122 and/or one or more external devices, and display information such as feedback to the rescuer 106 on a display 128.

In this example, rescuers 104, 106 are already in position and providing care to the victim 102, with rescuer 104 and providing chest compressions to the torso of the victim 102, and rescuer 106 providing ventilation using ventilation bag 112. The rescuers 104, 106 may be lay rescuers who were in the vicinity of the victim 102 when the victim 102 required care, or may be trained medical personnel, such as emergency medical technicians (EMTs). Although two rescuers are shown here for purposes of explanation, additional rescuers may also care for the victim 102.

Control and coordination for the resuscitation event and the delivery of the various therapies may be accomplished by a device or processing element that is external to the defibrillator 108, such as by use of a tablet-based computer that is controlled by one of the rescuers. For instance, the device may download and process ECG data from the defibrillator 108, analyze the ECG signals, perform relevant determinations based on the analysis, and control the other therapeutic devices. In other examples, the defibrillator 108 may perform all the processing of the ECG, including analyzing the ECG signals, and may transmit only the final determination of the appropriate therapy to a separate device, whereupon the separate device can perform the control actions on the other linked devices.

An electrode assembly 110 is shown on the victim 102 in a normal position. The electrode assembly 110, in this example, is an assembly that combines an electrode positioned high on the right side of the victim's torso, a separate electrode positioned low on the left side of the victim's torso, and a sensor package located over the victim's sternum. The sensor package, which, in this example, is obscured in the figure by the hands of rescuer 104 may include an accelerometer or similar sensor package that may be used in cooperation with a computer in the defibrillator 108 to monitor performance of the chest compressions.

The defibrillator 108 in this example is connected to the electrode package 110 and may operate in a familiar manner (e.g., to provide defibrillating shocks to the electrode package 110). As such, the defibrillator may take a generally common form, and may be a professional style defibrillator, such as the R-SERIES, M-SERIES, or E-SERIES from ZOLL Medical Corporation of Chelmsford, Mass., or an automated external defibrillator (AED), including the AED PLUS, or AED PRO from ZOLL Medical Corporation.

The defibrillator or a computing device associated with the defibrillator communicates wirelessly with the wrist-worn devices 120, 122, the wearable computing devices 125, 127 or other types of wearable computing devices to present information to the rescuers. For example, information can be visually presented on the displays 121, 123, 128. Additionally, vibrators or audible sound generators on the wrist-worn devices 120, 122, the wearable computing devices 125, 127, etc. can provide feedback. Such feedback, as discussed more fully below, may include information about physical status of the victim 102 and performance of CPR.

The wrist-worn devices 120, 122 can be smart watches (e.g., computerized wristwatches with functionality enhanced beyond timekeeping). Such a smart watch can effectively be a wearable computer. The smart watch can include a data processor, memory, input, and output. The smart watch collects information from internal sensors. It may control or retrieve data from other instruments or computers. For example, the smart watch can support wireless technologies, like Bluetooth and/or Wi-Fi, to communicate with the defibrillator 108 or another computing device. In some cases, the defibrillator 108 or another computing device can, automatically or in response to a user input and/or request, determine if a wearable computing device or another computing device is nearby, and establish a communication link with the wearable computing device or another computing device in response to that determination. In some examples, the smart watch may also serve as a front end for a remote system and be configured to display information generated by the defibrillator or associated computing device. For example, the smart watch and/or wearable computing device may be configured to display information from other instruments or computers, e.g., other wearable devices. In this example, the smart watch and/or wearable computing device can display information relating data collected by the internal sensors of other wearable computing devices, smart watches, instruments, and/or equipment. This feature can allow a user supervising the rescue efforts to use a wearable computing device, e.g., a watch, to monitor the multiple rescuers by receiving and displaying data captured by the personal computing devices of each rescuer.

The displays 121, 123 in the wrist-worn devices 120, 122 can be made of Indium gallium zinc oxide (IGZO), a semiconducting material, etc. IGZO thin-film transistors (TFT) can be used in the TFT backplane of flat-panel displays (FPDs). Because the IGZO display is flexible, a greater amount of information can be displayed on the wrist-worn devices 120, 122 due to the increased surface area of the display.

Along with being a pair of wearable glasses in some arrangements, the wearable computing devices 125, 127 can provide a variety of functionality and include various types of components. For example, the device interface 126 of the wearable computing device 127 can include one or more of the following: a data processor, memory, input, and output. The wearable computing devices can control or retrieve information from the wrist-worn devices 120, 122 or from other instruments or computers. In other examples, wearable computing devices may serve as a front end for a remote system and be configured to display information generated by the defibrillator or associated computing device. For example, the defibrillator 108 can send information about the performance of chest compressions, such as depth and rate information for the chest compressions to the wearable computing devices 125, 127. The wearable computing devices 125, 127 can also receive data from the other sensors associated with the victim 102 such as an airflow sensor provided with a ventilation bag. The wearable computing devices 125, 127 can also receive data from wrist-worn devices 120 and 122 worn by rescuers 104 and 106 respectively. The information from wrist-worn devices watches 120 and 122 can include information about the fatigue level of the rescuer (e.g., as described herein). In some examples, the wearable computing devices 125, 127 are configured to display information and provide feedback about the CPR performance of the user wearing the glasses. In other examples, the wearable devices 125, 127 can additionally or alternatively display information and feedback relating to multiple rescuers, e.g., rescuers 104, 106, or display information and feedback pertaining to another rescuer. In these examples, wearable computing device 127, for example, can display information and provide feedback relating the performance of the rescuer 106, to both rescuers 104 and 106 respectively, and/or relating to the rescuer 104.

A wearable computing device can provide the functionality of receiving, transmitting, and/or displaying data. Data processing may also be provided by such a wearable computing device (e.g., processing received data prior to display, processing data prior to sending to another computing device, etc.). In some instances, a wearable computing device can take the form of a head-mounted device that can include frame elements including lens-frames, a center support, one or more lenses, and side supports (for securing the device to a user). The wearable computing device may additionally include an on-board computing system, a still or video camera (mountable to the device at various locations), speakers, etc. The on-board computing system may have the capability to communicate with other computing devices, systems, etc. external to the wearable computing device, e.g., through a wireless network connection, a short-range (e.g., Bluetooth) connection, a cellular connection, or another type of connection.

Various techniques may be employed to exchange information between the wearable computing device and the wearer. For example, the wearable computing device may include one or more displays that may be coupled to the device. Such a display may be formed on one lens or multiple lenses of the wearable computing device and may be configured to overlay computer-generated images, graphics, etc. in the user's view of the physical world. The display can be positioned at one or more locations of the lens or lenses, for example, at the center of one or more of the lens. In general, the display is controllable by the on-board computing system and is in communication with the computing system by employing one or more data transmission techniques (e.g., an optical waveguide or fiber, electrical conductor, etc.). In some arrangements, the frame of the wearable computing device can be similar to a frame of a pair of glasses (e.g., prescription glasses, sunglasses, reading glasses, etc.). In some instances, the lenses incorporated into the device may be less than a completely formed lenses typically included in eyeglasses. Due to the less than complete lens or lenses, the device may not include a lower frame portion typically used to secure a complete lens to the frame.

To interact with the wearable computing device, one or more techniques may be employed. For example, a touch-based input (e.g., a touchpad) may be incorporated to sense the position and movement of a user's finger by capacitive sensing, resistance sensing, or other techniques. Equipment (e.g., one or more acceleration sensors) may be incorporated to sense the movement of a portion of the user (e.g., the user's head). One or more microphones may also be incorporated into the device to collect audible signals (e.g., voice commands) from the user. Similar to sensing position and movement, the direction of a user's finger (interacting with the touch-based input), the level of applied pressure, etc. may be sensed by interacting with device input.

In some arrangements, the wearable computing device can provide networking functionality. For example, the wearable device can be used to provide a node of a network architecture (e.g., a node for a mesh network). As such, information can be exchanged with (e.g., transmitted to, received from) other network nodes (e.g., other wearable computing devices at nearby locations, mobile computing devices, medical devices such as defibrillating systems, wearable medical devices, etc.). In one arrangement, multiple members of an emergency response team may each be outfitted with a wearable computing device that provides a network node. By employing data transmission techniques (e.g., one or more network protocols), information may be shared among the wearable computing devices, e.g., so each member is provided the same information during the emergency or so that information can be exchanged among members during the emergency.

Such capabilities may be incorporated into other types of wearable computing devices, such as a timepiece (e.g., a watch), an ear piece, an article of clothing or protective medical gear, etc.

In some examples, the emergency medical technician can interact with a computing device in the form of a heads-up device 103. The heads-up device 103 may include a graphical display 105 by which information is reported to the emergency technician. In some cases, the graphical display 105 includes a transparent plane upon which an image and/or graphic can be projected. The graphical display 105 can be attached or removably attached to the heads-up device 103. The emergency technician may interact with the heads-up device 103 to enter data into the system 100, receive feedback about the ongoing rescue efforts, or to receive guidance about the ongoing rescue efforts. The heads-up device 103 may include a device interface 107 for executing operations such as coordinating with the other components of the heads-up device 103 (e.g., exchange information, control signals, etc.), controlling of user interfaces, applications executed by heads-up device 103, exchanging information with other devices (e.g., wirelessly communicate with other devices), etc.

The heads-up device 103 may be configured to provide information to the emergency technician while allowing the emergency technician to view the surrounding environment in a generally unobstructed manner. For example, the heads-up device 103 may be configured to overlay computer-generated images, graphics, etc. in the user's view of the physical world.

The heads-up device 103 may also include a wireless transceiver for communicating with a wireless network, such as a 3G or 4G chipset that permits long distance communication over cellular data networks, and further through the internet. In some examples, the heads-up device 103 is used in combination with one or more wearable devices.

To interact with the heads-up device 103, one or more techniques may be employed. For example, a touch-based input (e.g., a touchpad) may be incorporated to sense the position and movement of a user's finger by capacitive sensing, resistance sensing, or other techniques. Equipment (e.g., one or more acceleration sensors) may be incorporated to sense the movement of a portion of the user (e.g., the user's head or the user's hands). Specific user motions may be associated with specific inputs. For example, a specific motion may cause the device to power cycle. One or more microphones may also be incorporated into the device to collect audible signals (e.g., voice commands) from the user. Similar to sensing position and movement, the direction of a user's finger (interacting with the touch-based input), the level of applied pressure, etc. may be sensed by interacting with device input.

In some arrangements, the heads-up device 103 can provide networking functionality. For example, the heads-up device 103 can be used to provide a node of a network architecture (e.g., a node for a mesh network). In one arrangement, multiple members of an emergency response team may each be outfitted with a wearable computing device that also provides a network node. By employing data transmission techniques (e.g., one or more network protocols), information may be shared among the wearable computing devices and the heads-up device 103, e.g., so each member is provided the same information during the emergency or so that information can be exchanged among members during the emergency.

While the heads-up device 103 is generally described as a separate device, it may be attached or removably attached to another device. For example, the heads-up device 103 may be attached or removably attached to a portable defibrillator.

Figure 2A:
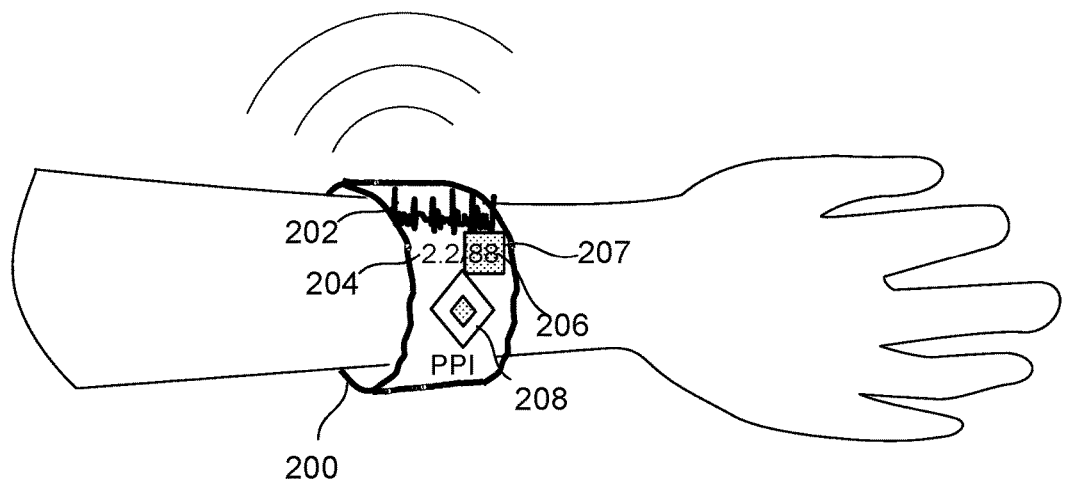
FIGS. 2A and 2B show exemplary smart watches displaying information associated with a rescue attempt.
Figure 2B:
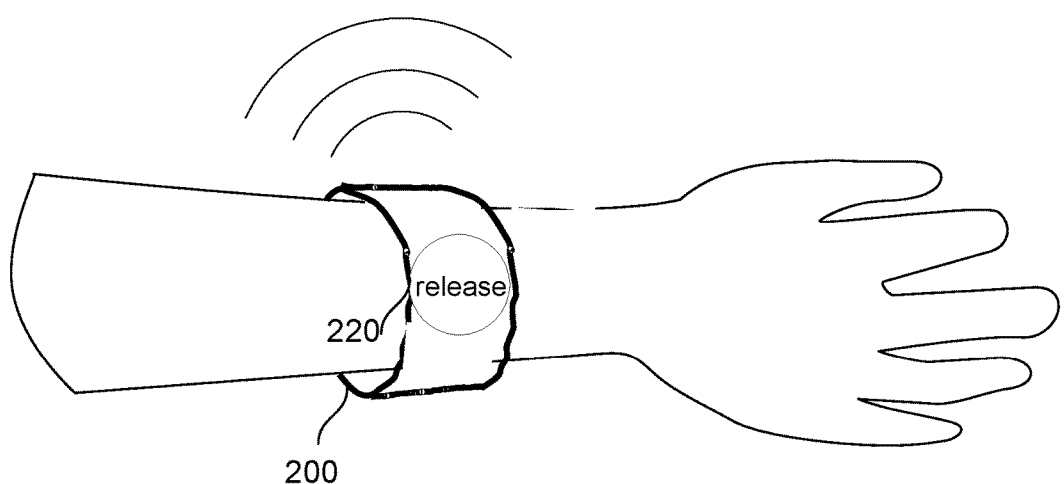

For illustrative purposes, two particular examples of feedback provided to a rescuer on the display of the wrist-worn devices are shown in FIGS. 2A and 2B.

As shown in FIG. 2A, a wrist-worn device 200 can provide information about the physiological state of the patient, as well as information about the quality of the CPR being performed by the rescuer. The wrist-worn device 200 includes a display for presenting CPR information. The CPR information may be automatically displayed when compressions are detected. The displayed information about the chest compressions can include rate of compressions 206 (e.g., number of compressions per minute) and depth of compressions 204 (e.g., depth of compressions in inches or millimeters). The rate and depth of compressions can be determined by analyzing accelerometer readings. Displaying the actual rate and depth data (in addition to, or instead of, an indication of whether the values are within or outside of an acceptable range) can provide useful feedback to the rescuer. A visual indicator 207, such as a color of the text or an applied highlighting, can be modified to indicate when a value for the depth and/or rate is outside of the preferred range. For example, if the rate of 88 compressions per minute as shown in FIG. 2A is too fast, the visual indicator 207 may include a red highlight indicating that the rescuer should slow down.

The displayed information about the chest compressions can also include a perfusion performance indicator (PPI) 208. The PPI 208 has a shape (e.g., a diamond) that is colored or shaded over time. The amount of the shape that is colored or shaded (e.g., the fill amount) provides feedback about both the rate and depth of the compressions. For example, when CPR is being performed adequately, the entire indicator may be filled. As the rate and/or depth decreases below acceptable limits, the amount of fill lessens. The PPI 208 provides a concise visual indication of the quality of the CPR such that the rescuer can aim to keep the PPI 208 completely filled.

In some implementations, the PPI 208 includes two axes—a vertical axis and a horizontal axis. The vertical axis may correspond to the depth of chest compressions, and the horizontal axis may correspond to the rate of chest compressions. For example, when the depth of chest compressions decreases below the acceptable limit, the fill amount of the PPI 208 in the vertical direction may be relatively small. Similarly, when the rate of chest compressions decreases below the acceptable limit, the fill amount of the PPI 208 in the horizontal direction may be relatively small. For example, if the depth of chest compressions is adequate but the rate of chest compression is below the acceptable limit, the fill amount of the PPI 208 may appear as a tall, thin diamond; if the depth of chest compressions is below the acceptable limit but the rate of chest compressions is adequate, the fill amount of the PPI 208 may appear as a short, wide diamond. Alternatively, the wearable device may further provide a score (e.g., a chest compression quality score) indicative of the overall quality in the performance of CPR which condenses multiple parameters/data (weighted or unweighted) monitored during the act of CPR and/or shortly thereafter, so as to improve future CPR. The chest compression quality score may be generated based on one or both of chest compression rates and chest compression depths.

The wrist-worn device 200 may be configured to display a filtered ECG waveform 202. In some examples, the filtered ECG waveform 202 can fill the entire span of the display. In some examples, other waveforms can also be displayed. For example, in some implementations, a second waveform (e.g., a $CO_2$ waveform, a volumetric $CO_2$ waveform, an $ETCO_2$ waveform, a $SpO_2$ waveform, etc.) is also displayed.

The data displayed by the wrist-worn device 200 can change based on the rescuer's actions. For example, the data displayed can change based on whether or not the rescuer is currently administering CPR chest compressions to the patient. In some examples, if multiple rescuers are present, this CPR information may be displayed to only the rescuer who is performing the CPR, and other information, such as patient data and/or ventilation feedback, may be provided to the other rescuers.

As shown in FIG. 2B, the wrist-worn device 200 can additionally or alternatively provide concise, simplified feedback with instructions to the rescuer regarding how to perform CPR. In this example, the wrist-worn device 200 provides a reminder 220 regarding "release" in performing chest compression. Specifically, a fatigued rescuer may begin to lean forward on the chest of a victim and not release pressure on the sternum of the victim at the top of each compression. This can reduce the perfusion and circulation accomplished by the chest compressions. The reminder 220 can be displayed when the system recognizes that release is not being achieved (e.g., signals from an accelerometer show an "end" to the compression cycle that is flat and thus indicates that the rescuer is staying on the sternum to an unnecessary degree).

In some examples, the wrist-worn device 200 can be configured to provide other types of feedback to the rescuer. The reminder 820 can be coordinated with other feedback, and can be presented in an appropriate manner to get the rescuer's attention. For example, the visual indication may be accompanied by vibration generated by the wrist-worn device 200 in order to indicate that a rescuer is to stop and modify how he or she is performing the CPR. For example, the wrist-worn device 200 may be provided with mechanisms for vibrating the device similar to mechanisms provided for vibrating portable communication devices (e.g., when an incoming telephone call is received on a smartphone). Such vibrating may be provided so as to alert the user to particular information and/or minimize the amount of information that can distract other rescuers in the area.

In some examples, the wrist-worn device 200 can generate periodic vibrations felt by the user to synchronize the chest compression activities with the desired rate. For example, the vibrations may be periodic occurring at the preferred chest compression rate (e.g., approximate 100 times per minute) to indicate when the rescuer 104 should be performing compressions. Such haptic feedback, when used to identify urgent information or provide instructions, may also relieve the rescuer 104 of having to constantly monitor the information displayed by the wrist-worn device 200. Thus, a first type of feedback, which may be (e.g., pulsed) visual, audible, or tactile, may be provided to signal the wearer of the wrist-worn device 200 to view information displayed on the wrist-worn device 200.

In some examples, the wrist-worn device 200 includes an audio output device such as a speaker for providing audible alerts and/or notification. The speaker may emit periodic tones to synchronize the chest compression activities with the desired rate. For example, the tones may be periodic occurring at the preferred chest compression rate (e.g., approximately 100 times per minute) to indicate when the rescuer should be performing compressions. In some examples, the audible alerts and/or notifications may be indicative of the rescuer's performance with regard to depth of chest compressions. For example, the speaker may provide spoken feedback to the rescuer (e.g., "push harder" or "push softer") if the rescuer is not administering the CPR appropriately.

In some examples, the wrist-worn device 200 includes a light (e.g., an LED) for providing visual alerts and/or notifications. The LED may emit periodic flashes of light to synchronize the chest compression activities with the desired rate. For example, the flashes of light may be periodic occurring at the preferred chest compression rate (e.g., approximately 100 times per minute) to indicate when the rescuer should be performing compressions. In some examples, the emitted light (e.g., the color of the emitted light) may be indicative of the rescuer's performance with regard to depth of chest compressions. For example, the LED may emit red light if the chest compressions are too hard (e.g., too deep), and the LED may emit a blue light if the chest compression are too soft (e.g., too shallow).

Two particular examples of feedback provided to a rescuer on the display of the wrist-worn devices 200 have been described above for illustrative purposes. However, similar feedback features may also be incorporated into the wearable computing devices 125, 127 of FIG. 1. For example, the display 128 may present a filtered waveform, a depth of compressions, a rate of compressions, a PPI, a visual indicator, and/or a reminder directed to the rescuer. In some implementations, the wearable computing devices 125, 127 include speakers and/or lights for emitting audible and/or visual notifications directed to the rescuer.

In some implementations, the wearable computing device can present feedback information via the display. The displayed information can include the rate of compressions (e.g., number of compressions per minute) and the depth of compressions (e.g., depth of compressions in inches or millimeters). Displaying the actual rate and depth data (e.g., in addition to or instead of an indication of whether the values are within or outside of an acceptable range) can provide useful feedback to the rescuer. A visual indicator (e.g., similar to the visual indicator 207 of FIG. 2A), such as a color of displayed text or an applied highlighting, can be modified to indicate when a value for the depth or rate is outside of the preferred range. For example, if the presented rate is too fast, the visual indicator may include a red highlight indicating that the rescuer should slow down.

The displayed information about the chest compressions can also include a perfusion performance indicator (PPI) (e.g., similar to the PPI 208). The PPI can have a shape (e.g., a diamond) that is colored or shaded over time. The amount of the shape that is colored or shaded (e.g., the fill amount) can provide feedback about both the rate and depth of the compressions. For example, when CPR is being performed adequately, the entire indicator may be filled. As the rate and/or depth decreases below acceptable limits, the amount of fill lessens. The PPI can provide a concise visual indication of the quality of the CPR such that the rescuer can aim to keep the PPI completely filled. As discussed further herein, the wearable computing device may also aggregate multiple parameters/data monitored during the act of CPR to provide a score (e.g., a chest compression quality score), where the individual parameters/data may be weighted or unweighted, to indicate to a user the overall quality in the performance of CPR, to improve the quality of future CPR.

The display of the wearable computing device may be configured to display a filtered ECG waveform. In some examples, other waveforms can also or instead be displayed.

In some implementations, the CPR feedback information may be related to a particular metric that has an unsatisfactory value (e.g., such that the chest compression quality score is negatively impacted by the metric). For example, if the depth of chest compressions has a satisfactory value but the rate of chest compressions is inadequate, the wearable computing device may provide feedback directed at the inadequate rate metric. The feedback may include a spoken message emitted by a speaker of the wearable computing device (e.g., "slow down" or "speed up"). The feedback may include a periodic vibration indicative of the desired rate of chest compressions, as described above with reference to the wrist-worn device 200 of FIGS. 2A-2B. The feedback may include a visual indicator, such as a light flashing at a rate that corresponds to the desired rate of chest compressions.

In some implementations, the wearable computing device may be configured to present the chest compression quality score and one or more calculated metrics to the rescuer. The one or more calculated metrics can correspond to a CPR component (e.g., chest compressions). Any combination of the chest compression quality score and the calculated metrics may be displayed continuously. Each of the calculated metrics may be presented in a way that corresponds to the impact that the particular metric has on the chest compression quality score. For example, calculated metrics that have a relatively negative impact on the chest compression quality score may be presented in bold text, and calculated metrics that have a relatively positive impact on the chest compression quality score may be presented in non-bold text. Similarly, if the chest compression quality score is unsatisfactory, it may be presented in bold text, and if the chest compression quality score is satisfactory, it may be presented in non-bold text. In this way, the rescuer can quickly determine whether the CPR is being adequately administered, and if not, the rescuer can quickly determine which of the CPR parameters additional attention should be afforded to.

By way of example, the chest compression quality score may be 86 (e.g., 86 out of 100). A score of 86 may be deemed satisfactory, and thus the chest compression quality score may be presented in non-bold text. However, there exists room for improvement of the chest compression quality score. The depth metric may have a satisfactory value, and thus may be presented in non-bold text. However, the rate metric may have an unsatisfactory value. Therefore, the rate metric may be presented in bold text. The bold text of the rate metric can serve to catch the rescuer's attention, and the rescuer can focus on improving the metric (e.g., by speeding up or slowing down the rate of chest compressions). Once the rate metric has a satisfactory value, the bold text may become unbolded and the chest compression quality score may increase accordingly.

Over time, the rescuer may become tired. As a result, the rescuer may be unable to attain a sufficient depth of compressions. Continuing with the example above, if the depth metric also assumes an unsatisfactory value, the chest compression quality score may decrease accordingly. If the chest compression quality score falls below a particular (e.g., predetermined) threshold, the chest compression quality score may be presented in bold text.

One or more other visual techniques may be employed instead of or in addition to the bold/non-bold text feature described above. For example, in some implementations, each of the calculated metrics may be presented as text having a color that correspond to the impact of the calculated metric on the chest compression quality score. For example, calculated metrics that have a relatively negative impact on the chest compression quality score may be presented in red text; calculated metrics that have a relatively neutral impact on the chest compression quality score may be presented in yellow text; and calculated metrics that have a relatively positive impact on the chest compression quality score may be presented in green text. In this way, the rescuer can quickly determine whether additional attention should be afforded to one or more of the CPR parameters. For example, a chest compression quality score having a value of 86 may be presented in yellow text, indicating that the chest compression quality score is within acceptable limits but there is room for improvement. The compression depth metric may be presented in green text and the compression rate metric may be presented in red text. Based on the text colors, the rescuer can quickly determine that the rate of compressions metric is unsatisfactory and is a major factor in the chest compression quality score being suboptimal.

In some implementations, feedback may be provided only when one or more aspects of the CPR performance is unsatisfactory. For example, if each of the calculated metrics falls within acceptable ranges and the chest compression quality score is acceptable, the wearable computing device (or, e.g., the wrist worn device 200 of FIGS. 2A-2B) may refrain from providing feedback to the rescuer so as not to distract the rescuer. In some implementations, positive feedback is provided to the rescuer, but such positive feedback may be minimal so as not to distract the rescuer.

While the wearable computing devices 125, 127 have been shown in the form of wearable glasses, other wearable computing devices having alternative configurations can also be used. For example, the wearable computing devices can include an exercise device and/or a mobile computing device such as a smartphone, a PDA, etc. that is configured to be worn on a hand, wrist, and/or arm of the rescuer. For example, the wearable computing device may be a smartphone that can be attached to or placed inside a band (e.g., a jogging band) to be worn by the rescuer. In some implementations, the wearable computing device is a fitness device (e.g., a pedometer) that can be clipped onto the clothing of the rescuer. The smartphone and/or the fitness device can be configured to operate in a manner similar to that described above with reference to FIGS. 1 and 2A-2B.

In some implementations (e.g., implementations in which the wearable computing device is a fitness device), the fitness device may also be configured to provide additional feedback to the rescuer related to the effort exerted by the rescuer while performing the CPR. The fitness device may be configured to provide recommendations to the rescuer for helping the rescuer improve the administered CPR without causing the rescuer to become overtired. For example, if the fitness device determines that the rescuer is exerting too much energy (e.g., based on the rescuer's vitals as measured by the fitness device), the fitness device may suggest that the rescuer adjust his or her posture, breathing, positioning, etc. Such feedback may be provided after the CPR has been administered, so as not to distract the rescuer during administration. In some implementation, the fitness device may present the rescuer with a score indicative of both the CPR performance and the rescuer's fitness performance during administration.

Figure 3:
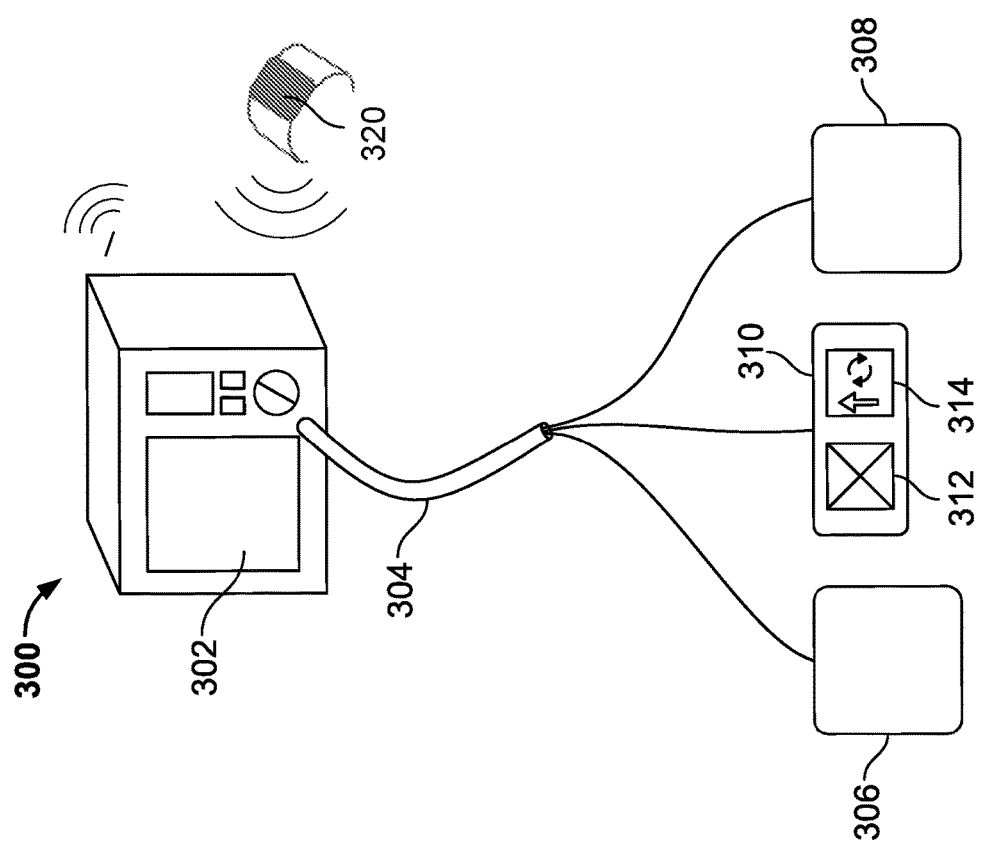
FIG. 3 shows a portable defibrillator and ancillary components arranged to provide feedback and instruction to rescuers.

FIG. 3 shows a portable defibrillator 302 and ancillary components arranged to provide feedback and instruction to rescuers via a smart watch 320. The smart watch 320 provides a display on which visual feedback can be provided to a rescuer at a location that is away from the defibrillator unit 302, and more immediately in the line of sight and focus of attention of a rescuer.

In system 300, the defibrillator 302 is connected to an electrode assembly by way of a wiring harness 304. The wiring harness 304 may include a number of wire leads and may be connected to the defibrillator 302 by way of a single plug. The wires may carry power from the defibrillator 302, such as current to provide a shock to a victim who is being provided with emergency care, or to the defibrillator 302, such as in the form of signals for generating ECG information, accelerometer information, and measurements of transthoracic impedance of a victim. The electrode assembly in this example includes a first electrode 306, a second electrode 308, and a chest compression assembly 310. The first electrode 306 may be configured to be placed above the victim's right breast, while the second electrode 308 may be configured to be placed below the victim's left breast. The chest compression assembly 310, in this example, includes a detector 312 and a display 314. The detector 312 may include a plastic housing within which an accelerometer assembly is mounted. The accelerometer assembly may move with the housing as chest compressions are performed on a victim so that motion of the accelerometer matches motion of the victim's sternum. The accelerometer in the housing may be connected to defibrillator 302 in order to pass signals through harness 304 (or may include a wireless transceiver for passing the information wirelessly). The defibrillator 302 may be provided with circuitry and/or software for converting such signals into the indications regarding the rate and depth of compressions being performed on the victim, in manners such as those described below. The display 314 may provide feedback that is directed to the rescuer who is performing chest compressions. In this example, the feedback can include similar feedback that is provided to the rescuer via the smart watch 320. For example, the display 314 can show feedback about CPR performance such as, an arrow indicating when the user is to perform chest compressions more vigorously and circular cycling arrows indicating when rescuers are to switch in performing chest compressions. In some examples, the accelerometer can be included in the watch 320.

The defibrillator 302 communicates with the smart watch 320 via a wireless connection. For example, the defibrillator 302 can communicate with the smart watch 320 using a wireless technology standard for exchanging data over short distances, such as Bluetooth technology, which uses short-wavelength radio transmissions in the ISM band from 2400-2480 MHz to form personal area networks (PANs) with high levels of security. Thus, the defibrillator 302 and the smart watch 320 each include a transmitter and a receiver for sending and receiving the wireless communications.

Figure 4:
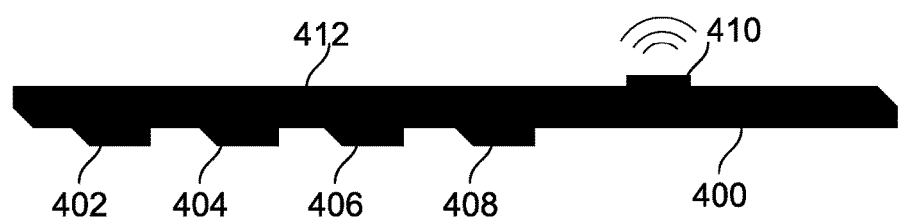
FIG. 4 shows an exemplary device including a display, sensors, and a communication module configured to be worn on the wrist of a rescuer.

FIG. 4 shows an exemplary smart watch 400 used to capture information from a rescuer and provide feedback to the rescuer via a display 412. One or more sensors can be used to capture information about the rescuer. When the rescuer places the smart watch 400 on his or her wrist, the one or more sensors are placed in contact with the rescuer's skin such that information about the physical state of the rescuer can be monitored. For example, the smart watch 400 can include a blood pressure sensor 402, a pulse oximetry sensor 404, and a colorimeter 408. In general, the pulse oximetry sensor 404 can be used to provide a (wirelessly) connected medical device, such as a defibrillator, with indications of the blood oxygen level and pulse rate of a rescuer wearing the device. In general, the blood pressure sensor can be used to provide a connected medical device, such as the defibrillator, with indications of the blood pressure of the rescuer. The colorimeter 408 is configured to obtain a spectra based on an intensity of light reflected primarily from the epidermis and dermal papillae of an individual's skin. The colorimeter 408 may take the form of a spectrophotometer, which generates spectral reflectance/absorbance data and provides a quantitative measurement of the reflection or absorption properties of a material as a function of wavelength. An exemplary colorimeter 408 is described in US patent publication number 2014/0378779, filed on Jun. 4, 2014, and titled "ANALYSIS OF SKIN COLORATION," the contents of which are hereby incorporated by reference in its entirety.

The smart watch 400 also includes a wireless transmitter/receiver 410. Information collected by the blood pressure sensor 402, pulse oximetry sensor 404, and colorimeter 408 can be sent to a remote processing device, such as a remotely located computing device, wearable computing device, or a computing device in a defibrillator via the wireless transmitter/receiver 410. Additionally, the smart watch 400 can receive information from the remotely located computing device or the computing device in the defibrillator via the wireless transmitter/receiver 410. The information received by the wireless transmitter/receiver 410 can be used to provide feedback to the rescuer about his/her performance during the rescue event. For example, the smart watch 400 can receive information to cause a display device 412 in the smart watch 400, a display in another type of wearable computing device, etc. to display information and feedback to the rescuer, such as the information and feedback described herein. Additionally, the smart watch 400, or another type of wearable computing device can receive commands to cause a tactile feedback device, such as a buzzer or vibration device 408, to provide additional stimulus to the user.

During use, the smart watch 400 is affixed around a user's wrist. The entire watch (including display 412) is flexible such that the display forms a curved surface and the various sensors located on the underside of the device will contact the rescuer's skin. In some examples, the smart watch 400 can include a band that is formed of layered, flexible stainless steel bi-stable spring bands sealed within a fabric or plastic cover. The display 412 is incorporated into a top surface of the band and the sensors 402, 404 and 406 are incorporated into a bottom or opposite surface of the band. The band can be straightened out, causing tension within the springy metal bands. The straightened bracelet is then slapped against the wearer's forearm, causing the bands to spring back into a curve that wraps around the wrist, securing the band to the wearer. Thus, no buckles or other fastening devices are required to secure the smart watch 400 to the rescuer's wrist. Rather, an applied force or pressure causes the band of the device to assume a shape that secures itself to the rescuers wrist. In some examples, the smart watch 400 can include a sensor or unit configured to sense when the smart watch 400 is secured to the rescuer's wrist (e.g., sense when the shape of the watch changes from being straight to being curved). The unit causes the smart watch 400 to turn on (e.g., apply power to the unit) upon sensing that the smart watch 400 has been secured to the rescuer's wrist. Thus, the wearer does not need to take additional actions to turn-on the smart watch 400 because the smart watch 400 turns on automatically upon modification of the shape of the band.

As described above, the smart watch device can include sensors that monitor the rescuer. Such values may then be used either independently or along with other factors, such as rate and depth of compressions, to determine when the rescuer should be instructed to stop performing chest compressions and yield to another rescuer. Also, the feedback provided to the rescuer on the smart watch or other type of wearable computing device can integrate information about rescuer blood oxygen level, pulse, or both in order to determine the feedback to be provided to the rescuer. Thus, for example, a processor in the wrist-worn device, a device interface of another type of wearable computing device, etc. may receive signals from the sensors and convert them partially or fully into blood oxygen and pulse rate values that can then be displayed or further processed (e.g., to identify that the rescuer is becoming fatigued).

Figure 5:
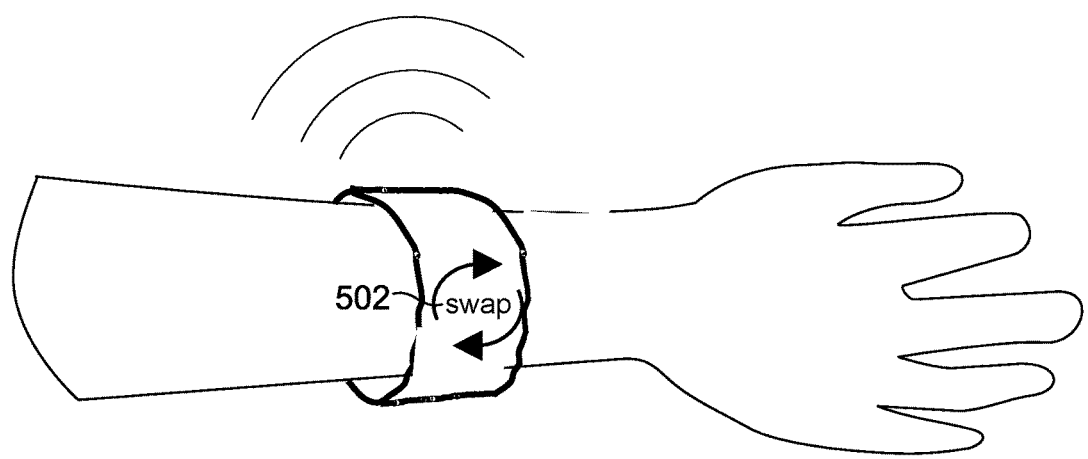
FIG. 5 shows an exemplary smart watch displaying an indication that the provider of care should change.

In one example, as shown in FIG. 5, feedback can be provided using a visual indicator on the smart watch indicating that the rescuer should change places with another rescuer. While the visual indicator is generally shown on the smart watch, the visual indicator can also be displayed on a display of a wearable computing device. In this example, cycling arrows 502 are displayed on the smart watch display screen. Such arrows may indicate to the rescuers that it is time for them to switch tasks. Using the example shown in FIG. 1, providing a rescuer swap indicator can indicate that that rescuer 104 should cease providing chest compressions and begin operating the ventilation bag 112 and rescuer 106 should cease controlling the ventilation and instead began providing chest compressions on electrode assembly 110. When there are three or more rescuers, the third rescuer may have been resting and can take over chest compressions for rescuer 104 when a rescuer change is directed by the system. The rescuer 104 may then rest or switch from providing chest compressions to providing ventilation assistance while rescuer 106 rests or does something else. The defibrillator may cause the cycling arrows 502 to be displayed based on the occurrence of various events. In one example, the cycling arrows 502 may be displayed after a set time period has elapsed since rescuer 104 began applying chest compressions. A particular CPR protocol may require switching of rescuers at certain predefined periodic intervals (e.g., every 2 minutes). As described previously as well as below in more detail, the cycling arrows 502, or a similar cycling signal, may alternatively be generated according to determinations made by the defibrillator regarding the level of rescuer fatigue. The defibrillator may thus be programmed to identify when factors indicate the rescuer's physical state (e.g., via pulse measurement) has started to decline. For example, a heart rate monitor in the smart watch can measure an increase in heart rate that may indicate fatigue by the rescuer and may be used to generate a signal to switch rescuers. A rescuer fatigue score can be calculated and compared to a threshold such that when the rescuer fatigue score exceeds the threshold, the system indicates that the rescuer should allow someone else to take over, by displaying cycling arrows 502, for example. In another example the system combines information about the length of time the rescuer has performed CPR with the rescuer fatigue information to determine a rescuer fatigue score.

Figure 6:
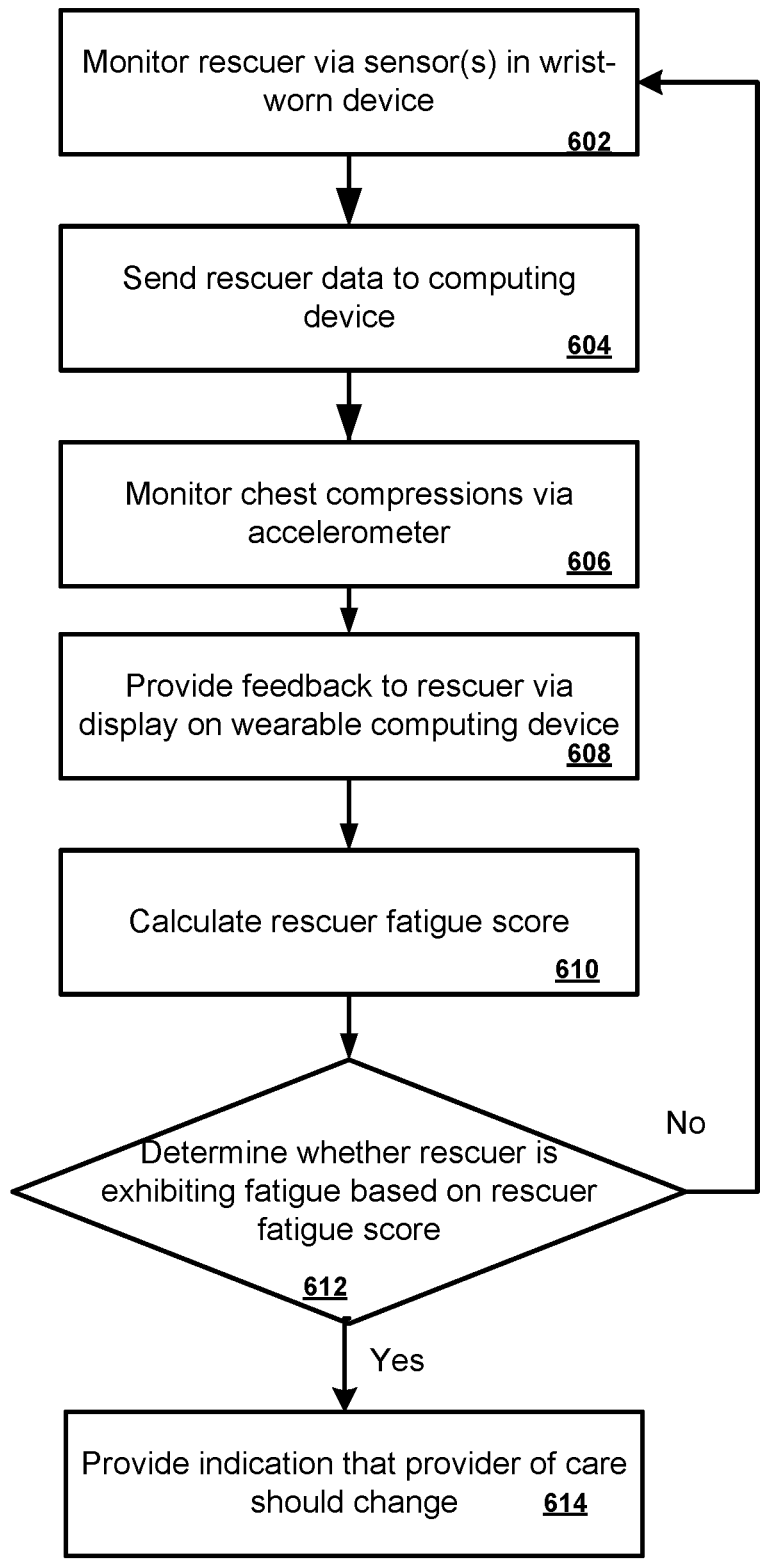
FIG. 6 is a flowchart of a process for monitoring rescuer status and providing an indication of when the provider of care should change.

FIG. 6 is a flowchart of a process for monitoring CPR performance and a rescuers physical state and providing feedback for improvement of the performance. Generally, the process involves automatic monitoring of the performance of a component of CPR, such as the provision of chest compressions to a victim, and providing an indication of when the provider/rescuer should stop performing the component and allow another rescuer to take over.

The process begins at box 602, where it monitors the physical state of the rescuer using various sensors included in a wrist-worn device. For example, the process can receive data indicative of one or more of the patient's blood pressure, heart rate, and inspired CO2. At box 604, this data is sent to a computing device. For example, the data can be sent from the wrist-worn device to a computing device in a defibrillator using a wireless protocol.

At box 606, the process monitors chest compressions via an accelerometer puck. For example, the rescuer may have applied the electrodes and the puck and have begun performing chest compressions on the victim. Such compressions may cause the puck to move and accelerate up and down, so that an accelerometer in the puck generates signals indicative of such acceleration. The defibrillator may receive such signals and convert them into indications of the quality of the chest compression, such as indications of how deep each chest compression is and the pace at which particular ones of the chest compressions are occurring.

At box 608, the process generates feedback related to the rescuer's performance of CPR and provides the feedback to the rescuer on a display of the wearable computing device. In some examples, the feedback can also be displayed on the smart-watch device. This information can include the depth and rate of chest compressions. Additionally, the feedback provided to the rescuer can include information about the patient status, such as a display of the ECG or SpO2 signaled.

At box 610, the process calculates a fatigue score based on the received rescuer monitoring data alone or in combination with the observed prior chest compressions. For example, the fatigue score may be computed as a function of the measured physical status of the rescuer. In another example the fatigue score may be computed as a function of the measured physical status of the rescuer in combination with the depth and rate of one or more chest compressions that have been observed from the accelerometer puck.

At box 512, a determination is made with regard to whether or not the fatigue score indicates a need to change the roles of the rescuers. For example, if a fatigue score is below a threshold that indicates an acceptable level of fatigue, the process returns back to box 502 and continues monitoring a rescuers physical status and the chest compressions using the accelerometer puck as well as determining the fatigue scores.

If the fatigue score exceeds the threshold indicating that the rescuer has begun to fatigue, at box 514, the process provides an indication to the rescuer, and perhaps to others, that a provider of care should change. For example, the smart watch can provide a visual indication that the provider of care should change. In addition, haptic feedback may be provided to the rescuer, such as switching from periodic (metronomic) vibration in a unit in the wrist-worn device to continuous vibration in the wrist-worn device, or another change in haptic feedback that differs from the feedback given when no change is to be made.

Using such a process, a system may then adjust to the capabilities of various caregivers and maintain caregivers in a position to provide a particular component of care as long as they are able to provide for it. As a result, the system need not be stuck to preset time limits that might not reflect the actual standard of care that can be adequately provided, but can instead vary based on the actual standard of care that is being given by a particular rescuer team in a particular situation. The process could result in better outcomes for victims tended to by such rescuers, and in a better experience for the rescuers themselves.

Figure 7:
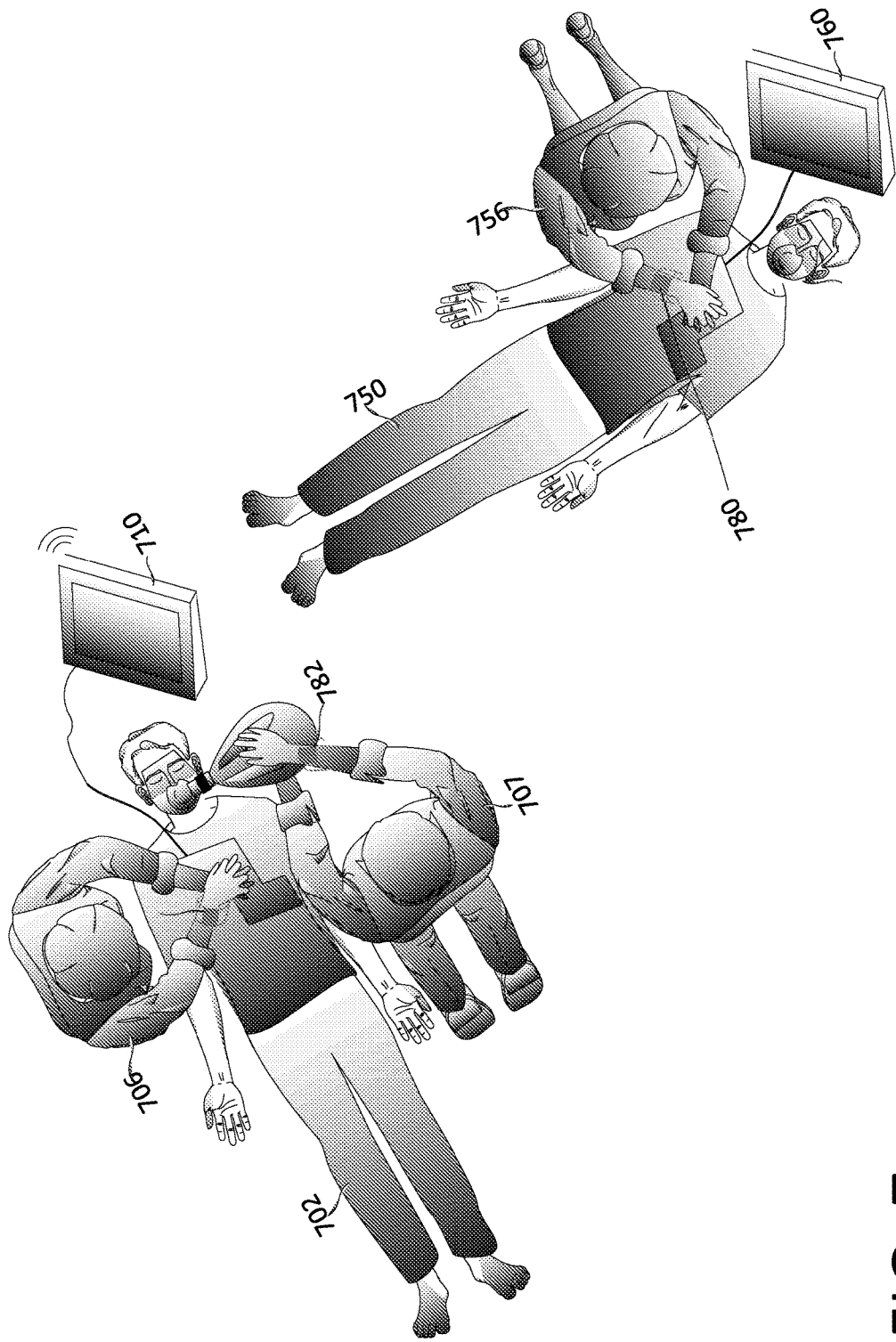
FIG. 7 is an overhead view of rescuers performing CPR on a victim using an electronic system that instructs them in their performance of the CPR.

In systems where smart watches or other types of wearable computing devices communicate wirelessly with a central computing device, such as the defibrillator, it is important to ensure that the smart watches or other devices are paired with the correct central computing device. For example, as shown in FIG. 7, at the scene of a mass casualty or mass rescue event, there can be multiple different patients 702, 750. It is essential that the smart watches or other types of wearable computing devices for a particular patient are correctly paired with the computing device or defibrillator associated with that patient. For example, the smart watches 784 and 782 should be wirelessly connected with the central computing element in defibrillator 710 while the smart watch 780 should be wirelessly connected to the central computing element in defibrillator 760. If, for example, the smart watches 784 and 782 associated with patient 702 were instead mistakenly wirelessly connected to defibrillator 760. The information displayed to the wearers would not be accurate. Additionally, the decisions of if/when to switch rescuers might be incorrect. In an extreme case, if patient 702 regained blood circulation and breathing and the sensors were mistakenly connected to the defibrillator 760, defibrillator 760 could erroneously instruct the rescuer 756 to discontinue administration of CPR on victim 750. In another example, if ECG information were erroneously transmitted to an incorrectly matched defibrillator, the defibrillator could erroneously shock a victim whose heart rhythm was non-shockable. In order to prevent such detrimental situations, it is important to ensure that the sensors are paired with the correct central computing device. While this pairing process is generally described with respect to the smart-watches, similar methods can be used to pair other types of wearable computing devices.

Correct pairing of a smart watch, other types of wearable computing devices, etc. with the patient-specific, localized network occurs when the smart watch is connected to the wireless network. Smart watches or other types of wearable computing devices (and thereby the rescuers) can join and leave various networks so that they can aid in different rescue attempts. For example, as rescuer 756 begins to fatigue, rescuer 706 might leave the rescue attempt for victim 702 and join the rescue attempt for victim 750. In doing so, the information displayed on the smart watch 782 worn by rescuer 706 should be changed to display the data for victim 750.

Various mechanisms can be used to allow a rescuer (and their smart watch, other type of wearable computing devices, etc.) to join/leave a particular network. For example, the smart watch can have a touch menu allowing the user to select a particular network from a list of networks. In another example, the smart watch can include mechanisms that allow a particular network to be selected based on actions of the user/watch without requiring the user to know and select the network. For example, a bump-to-join process could be executed in which, upon two smart watches contacting one another, the second smart watch joins the network of the first.

Figure 8:
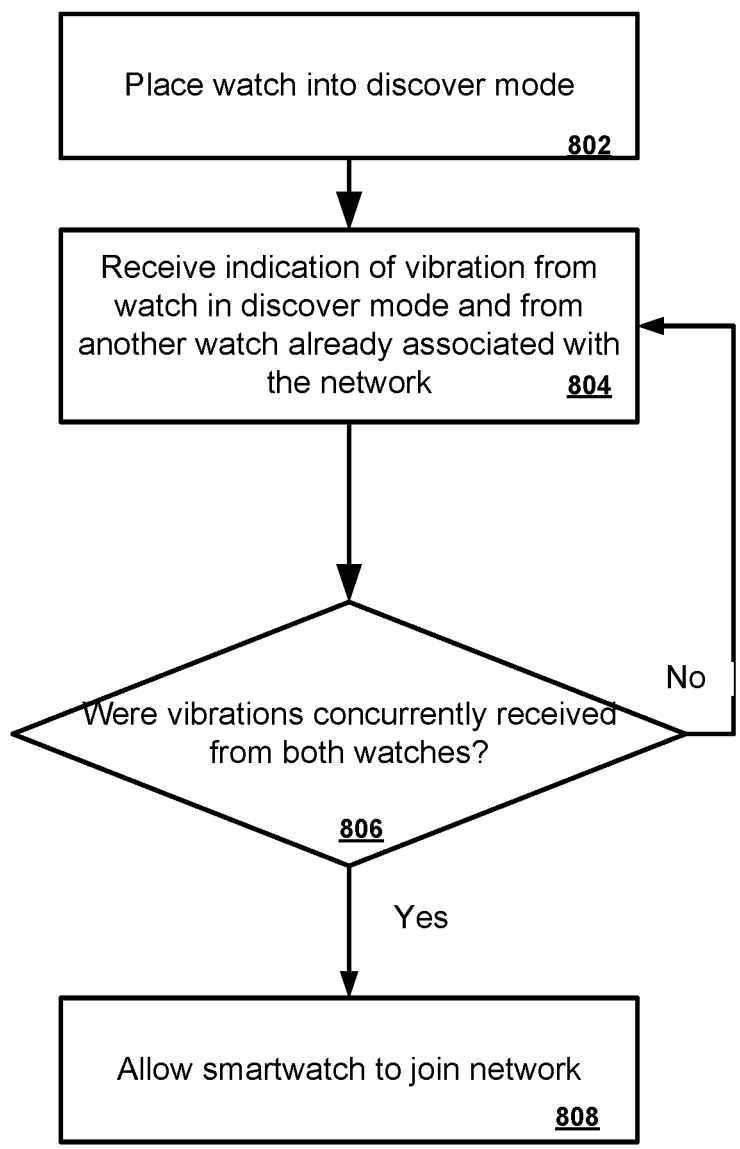
FIG. 8 is a flowchart of a process for joining a network.

FIG. 8 shows a process for adding a smart watch to a network associated with a particular defibrillator/patient. The process begins with a wearer of a smart watch desiring to join a particular network associated with a rescue attempt. The wearer places the smart watch into a discover mode (802). In the discover mode, the smart watch is granted/denied access to the network based on the concurrent receipt of signals from multiple smart watches. The concurrently received signals are indicative of the wearer's association with a particular rescue team. For example, in the scene of a mass rescue attempt where multiple different networks exist, the rescuer is connected to the correct network associated with the victim they will aid (e.g., as described in relation to FIG. 7) based on the concurrently received signals. The defibrillator or central computing device receives an indication of vibration from the watch in discover mode and from another watch already associated with the network (804). For example, each of the smart watches can include an accelerometer and the two wearers can shake hands or give a high five such that the accelerometers in each of the watches will concurrently measure a motion. The defibrillator or central computing device determines whether the vibrations were concurrently received from both watches (806). If the measured vibrations were concurrent, the system allows the smart watch in discovery mode to join the wireless network of the watch already associated with the network (808). Thus, a particular network is selected from amongst multiple different networks based on the network associated with the watch for which the concurrent signal was received. If the measured vibrations were not concurrent, the system returns to receiving vibration indications from the watch. While this pairing process is generally described with respect to the smart-watches, similar processes can be used to adding a wearable computing device to a network associated with a particular defibrillator/patient pair.

In some examples, a central management system can be connected to one or more smart watches and to other computing devices, e.g., other wearable computing devices, and the defibrillator associated with a patient rescue. As such, the central management unit can gather information about the rescue attempt and information about the rescuer performance.

Figure 9:
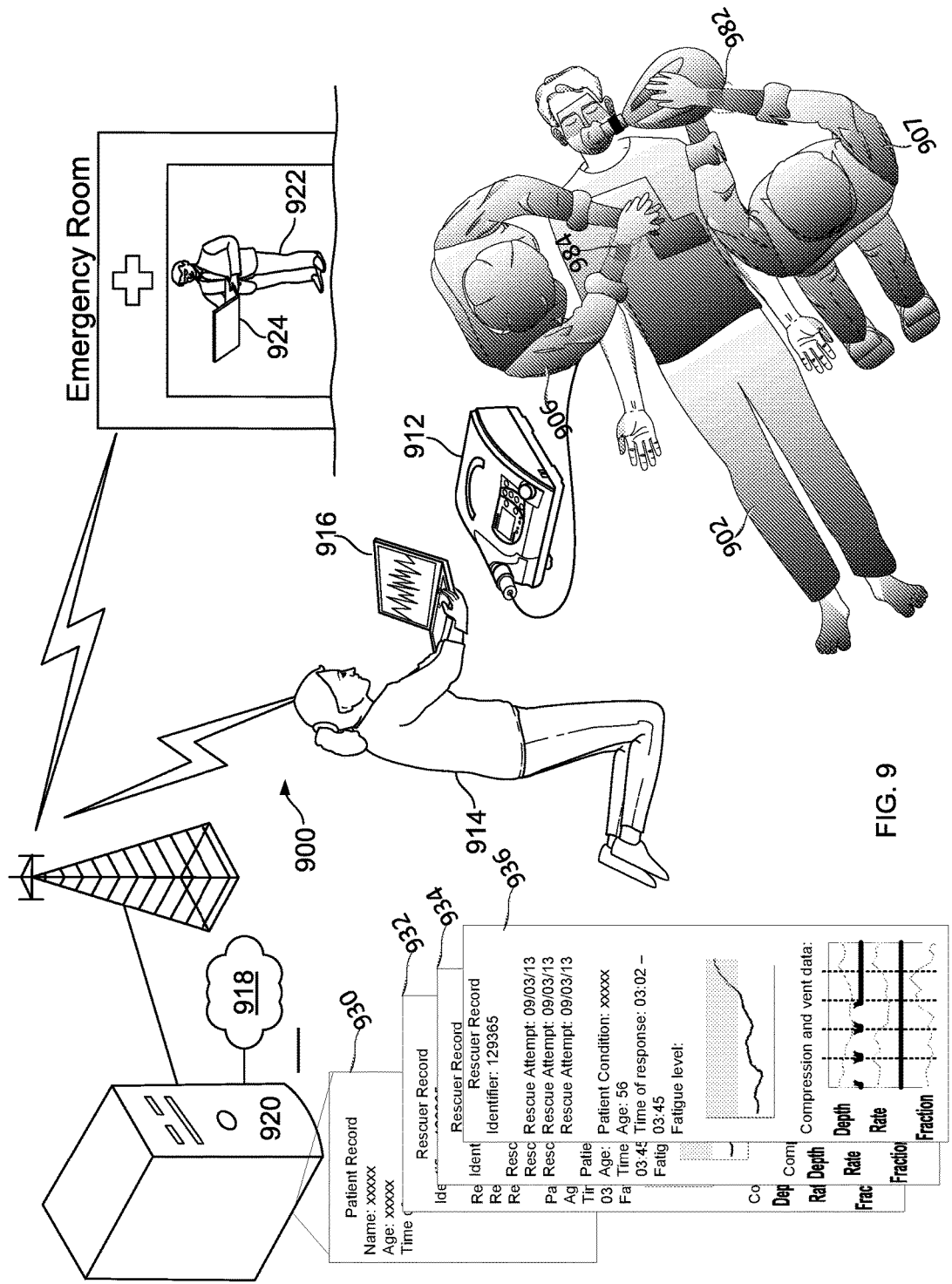
FIG. 9 is an overhead view of rescuers performing CPR on a victim using an electronic system that instructs them in their performance of the CPR.

In one particular example, FIG. 9 shows a system 900 for responding to an emergency medical condition of a victim 902. In general, system 900 includes various portable devices for monitoring on-site care given to the victim 902. The various devices may be provided by emergency medical technicians who arrive at the scene and who provide care for the victim 702, such as emergency medical technicians 906, 907 and 914. In this example, the emergency medical technician technicians 906, 907 and 914 have deployed several devices and are providing care to the victim 902. The emergency medical technician 914 in this example is interacting with a computing device in the form of a touchscreen tablet 916. In some examples, the emergency medical technicians 906, 907 and 914 may interact with a wearable computing device in the form of wearable glasses (as shown in FIG. 1). The tablet 916 may include a graphical display by which to report information to the emergency medical technician 914. A portable defibrillator 912 is shown in a deployed state and is connected to the victim 902. In addition to providing defibrillation, the defibrillator 912 may serve as a patient monitor via a variety of sensors or sensor packages. For example, as shown here, electrodes have been applied to the bare chest of the victim 902 and have been connected to the defibrillator 912, so that electrical shocking pulses may be provided to the electrodes in an effort to defibrillate the victim 902, and electrocardiogram (ECG) signals may be read from the victim 902. The defibrillator 912 may provide feedback in a conventional and known manner to a rescuer, such as emergency medical technician 914.

The defibrillator 912 may communicate through a short range wireless data connection with the tablet 916. The defibrillator 912 can provide to the tablet 916 status information, such as information received through the electrode assembly, including ECG information for the victim 902. Also, the defibrillator 912 can send information about the performance of chest compressions, such as depth and rate information for the chest compressions. The tablet 916 can also receive data from the other sensors associated with the victim 902 such as an airflow sensor provided with a ventilation bag. The tablet 916 can also receive data from smart watches 984 and 982 worn by rescuers 906 and 907 respectively. The information from smart watches 984 and 982 can include information about the fatigue level of the rescuer (e.g., as described herein).

A central server system 920 may communicate with the tablet 916 or other devices at the rescue scene over a wireless network and a network 918, which may include portions of the Internet (where data may be appropriately encrypted to protect privacy). The central server system 920 may be part of a larger system for a healthcare organization in which medical records 932 are kept for various patients in the system. Information about the patient 902 may then be associated with an identification number or other identifier, and stored by the central server system 920 for later access. Additionally, the central server system 920 may store records 932, 934, 936 that include information associated with each of the rescuers for various rescuers in the system. Information about the each of the rescuers may then be associated with an identification number or other identifier, and stored by the central server system 920 for later access. This information can include each rescue attempt in which the rescuer participated and their role in the rescue. Additionally, the information about the rescuer can include information about his/her fatigue level which is received from the smart watch, other types of wearable computing devices, etc. worn by the rescuer.

Other users may then access the data in the central server system 920. For example, as shown here, an emergency room physician 922 is operating his or her own tablet 924 that communicates wirelessly, such as over a cellular data network. As such, the physician 922 may review the data from central server system 920. In this manner, the system 900 permits various portable electronic devices to communicate with each other so as to coordinate care that is provided to a victim 902. In addition, the system 900 allows the technician 914 and others to see raw real-time data and derived real-time or historical data about a rescue attempt.

In some implementations, other data provided by wrist-worn devices (e.g., the wrist-worn devices 200, 202 of FIGS. 2A and 2B), including the calculated CPR metrics and/or feedback information described above, may also be provided to the central server system 920 and accessed by other users, such as the emergency room physician 922. Such data may also or alternatively be provided by the smart watches 922, 924. The data may be provided in real time. For example, the calculated CPR metrics and/or the feedback information can be provided and accessed in real time such that remote medical personnel can continuously monitor the administration of the CPR to verify proper compliance. The calculated CPR metrics may include a score (e.g., a chest compression quality score) indicative of the overall quality in the performance of CPR which may aggregate multiple parameters/data monitored during the act of CPR and/or shortly thereafter.

Many other implementations other than those described may be employed, and may be encompassed by the following claims.

What is claimed is:

1. A medical system for assisting a rescuer in resuscitation of a patient comprising:
   a head mounted device comprising a visual display;
   a chest compression sensor including one or more accelerometers configured to sense motion associated with cardio pulmonary resuscitation (CPR) chest compressions and to generate one or more signals indicative of chest motion;
   a wrist-worn device configured to be disposed on a wrist of the rescuer administering cardiopulmonary resuscitation (CPR) chest compressions, the wrist-worn device comprising one or more sensors configured to monitor at least one physical parameter of the rescuer;
   a patient monitor having at least one processor communicatively coupled to the chest compression sensor, the wrist-worn device, and the head mounted device, the at least one processor configured to:
      receive at least one of (i) the one or more signals indicative of the chest motion from the chest compression sensor and (ii) the at least one physical parameter of the rescuer from the wrist-worn device,
      analyze at least one of (i) the one or more signals indicative of the chest motion from the chest compression sensor and (ii) the at least one physical parameter of the rescuer from the wrist-worn device, and
      determine at least one of whether a quality of the chest compressions has deteriorated, and whether a physical status of the rescuer has declined, and
      display on the head mounted device, visual feedback comprising an indication of at least one of the deterioration in the quality of the chest compressions, and the decline of the physical status of the rescuer.

2. The system of claim 1, wherein the patient monitor provides an indication to switch rescuers based on at least one of the deterioration in the quality of chest compressions, and the decline in the at least one physical parameter of the rescuer, wherein the deterioration in the quality of chest compressions is based on the determination of whether the at least one chest compression parameter is outside of an acceptable range.

3. The system of claim 1, wherein the head mounted device includes wearable glasses.

4. The system of claim 3, wherein the display is formed on at least one lens of the wearable glasses.

5. The system of claim 3, wherein the wearable glasses include a camera to capture the specific rescuer motions of the rescuer.

6. The system of claim 1, wherein the at least one physical parameter of the rescuer includes at least one of a heart rate, blood oxygen saturation, and a blood pressure of the rescuer.

7. The system of claim 1, wherein the patient monitor is part of an external defibrillator.

8. The system of claim 1, wherein the wrist-worn device comprises a memory configured to store a unique identifier associated with the wrist-worn device.

9. The system of claim 1, wherein the wrist-worn device is configured to power on when the wrist-worn device wraps around the wrist.

10. The system of claim 1, wherein the display of the head mounted device is configured to present the visual feedback via a projected image.

11. The system of claim 1 wherein the at least one chest compression parameter includes a CPR compression depth and a CPR compression rate.

12. The system of claim 1 wherein the determination of whether the quality of the chest compressions has deteriorated includes configuring the at least one processor to determine incomplete release of the CPR chest compressions based on a detection of continued pressure on the sternum of the patient during a chest compression cycle.

13. The system of claim 1 wherein the head mounted device provides a communications network node in a communications network comprising a plurality of wearable computing devices corresponding to a plurality of emergency response team members.

14. The system of claim 13 wherein the plurality of wearable computing devices corresponding to the plurality of emergency response team members comprises one or more of one or more wrist-worn devices and one or more head mounted devices.

15. The system of claim 1, further comprising one or more physiological sensors associated with a patient and configured to provide one or more signals indicative of physiological information for the patient, wherein the one or more signals includes information of at least one of heart rate and inspired oxygen of the patient.

16. The system of claim 1 wherein the head mounted device includes a touchscreen configured to receive input from the rescuer.

17. The system of claim 1 wherein the head mounted device includes a microphone configured to receive voice commands from the rescuer.

18. The system of claim 1 wherein the head mounted device provides a communications network node in a communications network comprising one or more of a plurality of head mounted devices and a plurality of patient monitors.

19. The system of claim 1 wherein the head mounted device is configured to removably attach to a portable defibrillator.

20. The system of claim 1 wherein one or more of the patient monitor and the head mounted device are configured to transmit information to a central management system using a wireless network.

21. The system of claim 20, wherein the wireless network includes at least one of a cellular data network and Wi-Fi network.

22. The system of claim 1 wherein the head mounted device is configured to be disposed on the head of a rescuer not administering the CPR chest compressions, the head mounted device comprising:
   a device interface configured to receive the one or more signals indicative of the chest motion and the at least one physical parameter of the rescuer from the patient monitor; and
   a display to display the at least one physical parameter of the rescuer and the one or more signals indicative of the chest motion to the rescuer not administering the CPR chest compressions.

23. The system of claim 1, wherein the head mounted device includes one or more sensors for capturing specific rescuer motions.

24. The system of claim 23, wherein the specific rescuer motions are associated with causing the head mounted device to power cycle.

25. The system of claim 23, wherein the specific rescuer motions include detecting specific head movements or specific hand movement of the rescuer.

26. The system of claim 1, wherein the visual feedback includes at least one of depth and rate of the chest compressions performed by the rescuer.

27. The system of claim 26, wherein the visual feedback further includes a perfusion performance indicator that fills over time to provide an indication about depth and rate of the chest compressions.

28. The system of claim 26, wherein the visual feedback further includes a perfusion performance indicator that fills over time to provide an real-time indication about depth and rate of the chest compressions.

29. A method for assisting a rescuer in resuscitation of a patient implemented on at least one processor, comprising:
generating, by a chest compression sensor that includes one or more accelerometers, one or more signals indicative of a chest motion associated with cardiopulmonary resuscitation (CPR) chest compressions;
monitoring, by a wrist-worn device, at least one physical parameter of the rescuer;
determining at least one of whether a quality of the chest compressions has deteriorated, and whether a physical status of the rescuer has declined,
wherein the determination of whether the quality of the chest compressions has deteriorated includes:
receiving the one or more signals indicative of the chest motion from the chest compression sensor,
analyzing the one or more signals to determine at least one chest compression parameter, and
wherein the determination of whether the physical status of the rescuer has declined includes:
receiving the at least one physical parameter of the rescuer from the wrist-worn device, and
analyzing the at least one physical parameter to provide an indication of the physical status of the rescuer, and
displaying on a head mounted device, visual feedback comprising an indication of at least one of the deterioration in the quality of chest compressions, and the decline of the physical status of the rescuer.

30. The method of claim 29, further comprising generating an indication to switch rescuers in response to the at least one processor of the patient monitor determining the quality of the chest compressions has deteriorated or the physical status of the rescuer has declined, wherein the determination of whether the quality of the chest compressions has deteriorated includes determining whether the at least one chest compression parameter is outside of an acceptable range.

31. The method of claim 29 wherein the wrist-worn device comprises one or more sensors configured to monitor at least one of a heart rate, blood oxygen saturation, and a blood pressure of the rescuer.

32. The method of claim 29 wherein the patient monitor comprises an external defibrillator.

33. The method of claim 29, further comprising displaying on the display of the head mounted device a reminder for the rescuer to release during the CPR chest compressions.

34. The method of claim 33, further comprising displaying on the display of the head mounted device an indication of an incomplete release during CPR chest compressions in response to a detection of continued pressure on the sternum of the patient during a chest compression cycle.

35. The method of claim 29 wherein the head mounted device comprises wearable glasses.

36. The method of claim 35 comprising displaying the visual feedback on at least one lens of the wearable glasses.

37. The method of claim 29 comprising providing a communications network node in a communications network comprising a plurality of wrist-worn and head mounted devices corresponding to a plurality of emergency response team members.

38. The method of claim 29, further comprising receiving one or more signals indicative of physiological information for the patient, the one or more signals including information of at least one of heart rate and inspired oxygen of the patient.

39. The method of claim 29 comprising transmitting information to a central management system.

40. The method of claim 29 wherein the head mounted device is configured to be disposed on the head of a rescuer not administering the CPR chest compressions, the method comprising:
receiving, at the head mounted device, from the patient monitor, the at least one physical parameter of the rescuer and the one or more signals indicative of the chest motion; and
displaying, to the rescuer not administering the at least one physical parameter of the rescuer and the one or more signals indicative of the chest motion of the rescuer administering the CPR chest compressions.

* * * * *